US006552783B1

(12) United States Patent
Schmidt et al.

(10) Patent No.: US 6,552,783 B1
(45) Date of Patent: Apr. 22, 2003

(54) OPTICAL SYSTEM

(75) Inventors: Peter E. Schmidt, Newtonville, MA (US); Pamela R. Lipson, Cambridge, MA (US); John C. Bowman, Lexington, MA (US)

(73) Assignee: Teradyne, Inc., Boston, MA (US)

( * ) Notice: Subject to any disclaimer, the term of this patent is extended or adjusted under 35 U.S.C. 154(b) by 114 days.

(21) Appl. No.: 09/605,613

(22) Filed: Jun. 28, 2000

(51) Int. Cl.[7] .............................................. G01N 21/88
(52) U.S. Cl. ................................................... 356/237.4
(58) Field of Search ........................... 356/237.4, 237.5

(56) References Cited

U.S. PATENT DOCUMENTS

| | | | |
|---|---|---|---|
| 4,894,790 A | | 1/1990 | Yotsuya et al. |
| 4,959,898 A | * | 10/1990 | Landman et al. ............. 29/705 |
| 5,008,743 A | | 4/1991 | Katzir et al. |
| 5,032,735 A | * | 7/1991 | Kobayashi et al. .... 250/559.34 |
| 5,058,982 A | * | 10/1991 | Katzir ......................... 385/33 |
| 5,187,611 A | | 2/1993 | White et al. |
| 5,450,201 A | | 9/1995 | Katzir et al. |
| 5,542,600 A | | 8/1996 | Kobayashi et al. |
| 5,619,429 A | | 4/1997 | Aloni et al. |
| 5,619,588 A | | 4/1997 | Yolles et al. |
| 5,684,530 A | * | 11/1997 | White ......................... 348/131 |
| 5,699,447 A | | 12/1997 | Alumot et al. |
| 5,745,236 A | | 4/1998 | Haga |
| 5,764,536 A | | 6/1998 | Yamamoth et al. |
| 5,793,901 A | | 8/1998 | Matsutake et al. |
| 5,982,493 A | | 11/1999 | Lehnen et al. |
| 5,987,191 A | | 11/1999 | Suzuki |

FOREIGN PATENT DOCUMENTS

| | | |
|---|---|---|
| EP | 0 822 409 A2 | 1/1997 |
| WO | WO 00/10114 | 2/2000 |

OTHER PUBLICATIONS

International Search Report of PCT Application No. PCT/US01/19987 dated Jan. 31, 2002.
: Toh, Peng Seng; U.S. patent application Publication Pub. No.: US 2001/0012107 A1, Pub. Date: Aug. 9, 2001; Entitled: "Method and Apparatus for Inspecting a Printed Circuit Board Assembly;" U.S. patent application No.: 09/761,263, filed On: Jan. 16, 2001; Assigned to Agilent Technologies.

* cited by examiner

Primary Examiner—Richard A. Rosenberger
(74) Attorney, Agent, or Firm—Daly, Crowley & Mofford, LLP (57) ABSTRACT

An optical system for use in an inspection system is described. The optical system includes an imaging system which may be provided as a multi-spectral band pass image recording system and a lighting system which includes at least one coaxial light and at least one side light to provide spectral discrimination and to provide contrast between a first surface made from a first material and a second surface made from a second different material.

40 Claims, 2 Drawing Sheets

OPTICAL SYSTEM

STATEMENTS REGARDING FEDERALLY SPONSORED RESEARCH

Not applicable.

CROSS-REFERENCE TO RELATED APPLICATIONS

Not applicable.

FIELD OF THE INVENTION

This invention relates generally to optical systems and more particularly to optical systems for use with inspection of printed circuit boards.

BACKGROUND OF THE INVENTION

As is known in the art, many systems for inspecting assembled printed circuit boards (PCBs) typically use black-and-white charge coupled device (CCD) cameras. With only black-and-white images, the detection of certain classes of component becomes impossible or highly unreliable at best, such as the detection of a black component on a dark green PCB. Such difficulties result in systems having relatively high false detection rates, with undesirable results for the customer. For example, a PCB with 1000 components is not unusual, but a false rate of only 1/1000 means that 63% of PCBs will have at least one inspection error.

Neither PCBs nor components are fabricated with machine vision inspection in mind. Thus, the variety of PCB and component materials and surface appearance pose additional difficulties for black-and-white imaging systems.

To further complicate the inspection process, there is a large variation in the location and shape of component orientation marks. This can make the orientation marks difficult to detect without some optimized lighting. The variation in appearance even extends to fiducials, which provide the coordinate system for the PCB. So-called Hot Air Solder Leveled (HASL) fiducials are common and have an irregular shaped dome-like appearance which makes them difficult to find accurately with the lighting in many inspection systems. This in turn makes accurate position measurements of the components on the PCB difficult.

It is a known principle in optics that the angle of illumination of an object influences both the intensity and spectral distribution of the reflected light. If one could optically model the surface of an object, it would be possible to predict the spectral distribution and intensity of light reflected by the object. The surfaces of real objects having irregular shapes, however, are so complicated that modeling the surfaces is relatively difficult and in some cases may not be possible.

To distinguish between two objects or between two different surfaces of the same object, some inspection systems use color lights for inspection. Such systems typically include a bank of different color light sources. For each object type, a particular color light source projects a light that maximizes the contrast of a surface of the object and another surface. For example, in printed circuit board inspection systems, a particular color light source projects a light that maximizes the contrast of a surface of a component and a surface of a printed circuit board on which the component is disposed. One problem with such systems, however, is that they require several light sources each of which projects a different color light. Moreover, a system user must know which color light to used for each different type of object or component.

It would, therefore, be desirable to provide an optical system which improves the ability to detect PCB components, fiducials and other PCB features with a relatively high degree of accuracy. It would also be desirable to provide a relatively simple optical system to distinguish between two objects or between two different surfaces of the same object.

SUMMARY OF THE INVENTION

In accordance with the present invention, an optical system includes an imaging system and a lighting system. The imaging system utilizes spectral reflectivity to discriminate between electronic components (components) to be inspected and a surface of the printed circuit board (PCB) on which the components have been placed. The lighting system includes a first light source disposed to project diffuse light along or coaxial with an optic axis of the imaging system and a second light source or sources disposed to project diffuse light from a position which is to the side of the object to be inspected.

With this particular arrangement, an imaging system which provides good discrimination between an object to be inspected (e.g. an electrical component) and a second object (e.g. a surface of a printed circuit board in which the object is disposed) is provided. The purpose of the diffuse coaxial lighting is to illuminate metallic surfaces on the PCB (including but not limited to HASL fiducials, pads of component footprints, component leads, etc.) so that specular highlights are minimized. For this purpose, "diffuse" means that the light rays from the coaxial lighting be incident on these metallic surfaces at angles of zero to at least 10 degrees with respect to the optic axis. This lighting, although very effective for its stated purpose, provides little discrimination between the components and the surface of the PCB on which the components are to be disposed (e.g., PCB material FR4 with solder mask). This is due to the optical reflection characteristics of the PCB surface.

The PCB reflection/optical characteristics of the PCB surface, mainly because of the solder mask characteristics, will vary from highly reflective (specular) to matte. The closer the reflection is to being specular, the less color information it carries, meaning that colored PCB surfaces will appear desaturated or neutral rather than colored. Thus, the system also includes diffuse lighting from the side, at a central angle typically in the range of about 30 to about 60 degrees with respect to the PCB surface and symmetrically placed about the optic axis. The illumination provided by the side lighting helps the camera distinguish the components from the PCB surface.

Because of the high reflectivity of the metallic surfaces on the PCB, the intensity of the coaxial illumination is selected to be lower than the intensity of the side illumination. Also, the spectral distribution of the coaxial light is selected to be significantly different from the spectral distribution of the side lighting. This can be achieved in several ways. For example, lights of different correlated color temperatures, or lights of similar correlated color temperatures combined with different spectral bandpass filters. This allows discrimination between footprint pads (reflective) and solder paste, which may or may not fully cover the pads, by measuring the spectral characteristic of the reflected light. Here "correlated color temperature" refers to visual appearance equivalent to a blackbody radiator at a given color temperature, as defined by CIE.

Having two types of lighting also provides flexibility for adjustment of side lighting angle and relative intensity for better detection of orientation marks on components.

The optical system lensing is chosen to be telecentric to avoid perspective effects and minimize the change in magnification with the height of the object viewed. This is very important for dimensional measurement on the assembled boards being inspected, where components can have substantially different heights.

Thus, advantageous features of the optical system of the present invention include: (1) spectral discrimination through the use of a combination of coaxial and side lighting; (2) recognition that diffuse side lighting provides good spectral discrimination between components and a PCB surface; (3) recognition that coaxial lighting and side lighting with a significantly different spectral distribution provides significant spectral discrimination between specular reflective surfaces (e.g., footprint pads) and diffusing surfaces (e.g., solder paste); (4) use of coaxial lighting intensity which is lower than the side lighting intensity.

In accordance with a further aspect of the present invention, an optical system includes an imaging system and a lighting system disposed about the imaging system. The lighting system includes a first light for providing diffuse illumination to a first region along an optical path approximately coincident with an optic axis of the imaging system and one or more second lights, each of the one or more second lights for providing diffuse illumination to the first region along a path which is at an angle with respect to the optical path of the color imaging system.

The imaging system can be provided as a multi-spectral band imaging system which includes a CCD color camera having a telecentric lens coupled thereto. The telecentric lens avoids perspective effects and the lighting provides not only spectral discrimination but contrast between metallic surfaces such as fiducials and the PCB surface, while minimizing specular highlights.

It should be appreciated that the light sources provided as part of the illumination system do not have to be different spectral distributions. That is, the spectral difference can come from the lights themselves or from identical lights plus a spectral filter. Thus, the light could be passed through different spectral bandpass filters. In one embodiment, a continuous fluorescent light is used. Fluorescent lights come in different correlated color temperatures. An alternative approach is to use two xenon strobe lights. The strobe lights would preferably be the same color, so spectral filters would be used.

For non-strobe lighting, the camera exposure typically needs to be tens of milliseconds. This would cause image blurring in a moving camera. Because of this, the motion system carrying the camera has to come to a stop and settle before the image can be acquired. The benefit of the strobe light approach is that because the duration of the strobe light pulse (typically tens of microseconds) is so short that the camera can be in rapid motion while the image is taken, without image blurring.

When illuminated from the top only, the surface of the printed circuit boards appears desaturated or neutral gray, thus the board does not look very different from the components on top of it. It has been recognized in accordance with the present invention that side lighting brings out the spectral reflection characteristic of the board. Recognizing that this difference results from use of both top and side illumination allows the system to spectrally discriminate between board and component.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

In the description herein below, reference is sometimes made to an inspection system having a particular imaging system or imaging system components or a particular lighting system or lighting system components or lights which operate at particular correlated color temperatures. Those of ordinary skill in the art will appreciate, of course, that the concepts described herein apply equally well to inspection systems having any type of imaging or lighting components provided that the components have the desired operational or functional characteristics. Reference is also sometimes made herein to a lighting system having lights disposed in a particular topology. Those of ordinary skill in the art will appreciate that the principles of the present invention can be implemented using a variety of light topologies and that those presented herein are only examples and should not be construed as limiting. It should be appreciated that relationships between the components (e.g. relative positions, relative spectral distributions and intensities) are typically relevant rather than any specific components or spectral distributons or values discussed herein. Thus, any set of components and topologies capable of implementing the desired inspection functions can be used.

Reference is also sometimes made herein to inspection of certain objects such as printed circuit boards and circuit components disposed on printed circuit boards. Those of ordinary skill in the art will appreciate that the principles of the present invention can find use in a variety of applications including, but not limited to, inspection of printed circuit boards and components, inspection of any other types of objects particularly where one object is disposed over and possibly in contact with or in close proximity with another object, art gallery and museum management, architectural image and design, interior design, remote sensing and management of earth resources, geographic information systems, scientific database management, weather forecasting, retailing, fabric and fashion design, trademark and copyright database management, law enforcement and criminal investigation and picture archiving and communication systems and that the embodiments presented herein are only examples and should not be construed as limiting.

Figure 1:
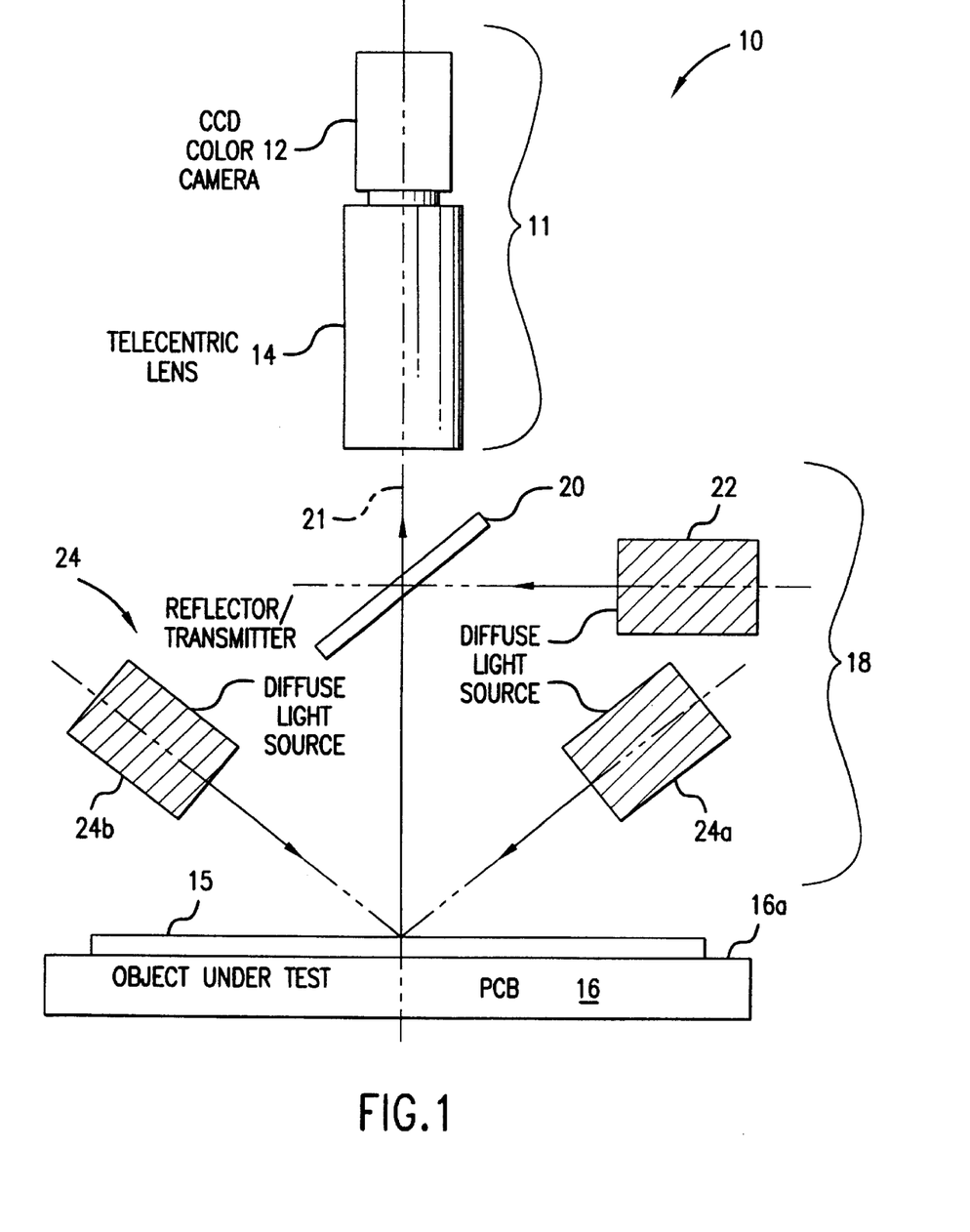
FIG. 1 is a block diagram of an optical system which includes a multi-spectral band imaging system and a lighting system which uses top and side lighting to enhance spectral discrimination between PCB, components, and solder paste, and contrast between metallic surfaces such as fiducials and PCB surfaces while also minimizing specular highlights.

Referring now to FIG. 1, an optical system 10 includes a color imaging system 11 and a light system 18. In one embodiment, the multi-spectral band imaging system 11 includes a charge coupled device (CCD) color camera 12 having a telecentric lens 14 coupled thereto. The CCD multi-spectral band camera 12 allows color to be used during an inspection process to discriminate between two objects in a field of view of the camera 12. The two objects may, for example, be provided as one or more electronic components 15 or other object or device to be inspected 15 (hereinafter components 15) and a printed circuit board (PCB) 16 on which the components 15 have been placed.

The camera 12 may be provided as the type manufactured by Basler AG, An der Strusbek 60–62, D-22926 Ahrensburg, Germany and identified as part number A113C. The camera may also be provided as the type manufactured by Roper Scientific MASD Inc., 11633 Sorrento Valley Road, San Diego, Calif. 92121, and identified as part number ES 1.0 MegaPlus Color.

Those of ordinary skill in the art will appreciate of course that other cameras having similar electrical and optical characteristics can also be used.

The optical system lensing is chosen to be telecentric to avoid perspective effects, i.e., to avoid or minimize change in magnification with the height of the object viewed. This is very important for dimensional measurement on the assembled boards being inspected,:where components can have substantially different heights. The telecentric lens may be provided, for example as the type manufactured by Melles-Griot Optical Systems, 55 Science Parkway, Rochester, N.Y. 14620 and identified as a Melles-Griot lens set: 59LGB485 base lens, 59LGH431 attachment lens, 59LGT101 F-to-C-mount adapter.

Those of ordinary skill in the art will appreciate of course that other telecentric lenses having similar magnification and other optical characteristics can also be used. It should be appreciated that in one particular embodiment, a magnification of 0.275 was used which gives a field of view of 1.29"×1.29" with the MASD camera. Other cameras will have different sensor sizes, and other applications might use a field of view of a different size; the magnification would then need to change correspondingly. For example, if the Basler camera is used with its different sensor size instead of the MASD, then it would be necessary to select a lens having a different magnification to get the same field of view.

It should be appreciated that it is important to use a telecentric lens or other system having telecentric properties lens since processing in accordance with the present invention is more complex than simple template-matching, and includes precision measurement. Components on the board have height, and their dimensions would change with height with non-telecentric optics 14. Because of the viewing angle at the side of the field of view, it's also possible for a top edge of a component to obscure board features. One might think that, by using the "known" height of a component, it would be possible to correct for sideways displacement due to perspective. It has been discovered in the present invention, however, that in fact, because of the tolerances in the height of components, this cannot be done accurately.

The PCB 16 may be provided from a material such as FR4, for example, with a solder mask. Those of ordinary skill in the art will appreciate that the concepts of the present invention apply equally well to inspection of PCBs 16 provided from any material well known to those of ordinary skill in the art including but not limited to FR4.

The optical system 10 further includes a lighting system 18 which includes a reflector/transmitter 20 disposed along an optical axis 21 of the camera system 11. In this particular embodiment, the reflector/transmitter 20 is disposed at an angle of about forty-five degrees with respect to the axis 21. A first diffuse lighting source 22 projects a diffuse light against the reflector/transmitter 20. The reflector/transmitter reflects the diffuse light along the optical axis 21. The diffuse light illuminates metallic surfaces (including but not limited to HASL fiducials, pads of component footprints, component leads) disposed on the PCB 16 so that specular highlights are minimized. This lighting, although very effective for its stated purpose, provides little discrimination between the components 15 and a surface 16a of the PCB because of the optical reflection characteristics of the PCB surface. This is true in the case where the PCB is provided from FR4 or from any other material having optical reflection characteristics similar to FR4.

To help overcome this problem, the system 18 includes a plurality of diffuse lighting sources generally denoted 24 disposed to the side of the optical axis 21. The particular number of lights selected for use in any particular application may vary depending upon the application. In general however, it is desirable to illuminate uniformly the region being inspected. It has been found in printed circuit board inspection applications that uniform illumination is best achieved by symmetric lighting. Thus, in one preferred embodiment, the side lights are symmetrically disposed about the optic axis.

For simplicity, only two such lights are shown in FIG. 1 (shown symmetrically disposed to the left and right about the optic axis, there would actually be four (also front and back). n other embodiments, however, fewer or more than four lights could be used. Also, the pattern in which the lights are disposed about the optic axis can aid in achieving the objective of uniform illumination. Two patterns which have been found to provide symmetric lighting are quadrangular and circular configurations.

In this particular embodiment, two lighting sources 24a, 24b are shown disposed to the side of the optical axis 21 at an angle in the range of about 30 degrees to about 60 degrees with respect to a plane which lies on the surface 16a. It should be appreciated that while angles outside of this range may also work, there is gradual degradation of system performance past these angles due to the consequent introduction of shadow, shading and other characteristics.

The lighting sources 24 are thus disposed symmetrically about the region being examined in a predetermined pattern. In a preferred embodiment, the light sources 24 are disposed symmetrically about the optical axis 21. Measurements demonstrate that side lighting implemented in this manner provides good discrimination between the components 15 and the surface 16a of the PCB 16.

It should be appreciated that in a preferred embodiment, it is desirable for the downward light to be more diffuse than the sideward light because the objects to be illuminated by the sidelight will themselves be diffusing.

The appropriate intensity of each of the center and side lights can be selected empirically or analytically such that appropriate levels of light are reflected from the surface being inspected and sensed by the camera. In one empirical approach to selecting the light intensities, the light source intensity levels are set and the light is projected at the inspection region. The camera (e.g. camera 12) senses the reflected light. The intensity of the center and side lights are adjusted until the camera senses sufficient light.

Generally, the camera senses sufficient light when the system is able to operate correctly. Sufficient light could be defined operationally by the camera sensor being able to view a standard spectrally neutral target (such as the Kodak 18% Gray Card) at a particular signal level at a reasonable exposure time and at a particular lens aperture of f/11 or smaller. For example in one embodiment with the camera, lens and light instruments described above, the signal level could be about 200 digits(on a scale of 0–255), at a reasonable exposure time of about 25 milliseconds, and at a lens aperture of f/11 or smaller. It should be appreciated that in other embodiments different values may be used.

It should be appreciated that contributing to the intensity seen by the camera are not only the strength of the lights themselves, but lens aperture, and reflecting/transmitting elements in the optic path, the camera exposure time and camera gain factor, as well as the sensor spectral sensitivity. Thus, once appropriate levels for top and side light intensities are selected, the ratio of top light compared to side light can be used over a range of absolute light values.

In one embodiment, the system uses one set of fluorescent lighting where the color spectrum difference is characterized by a correlated color temperature difference of about 2700° K. (warm fluorescent) to about 5100° K. (cool white fluorescent). In one embodiment the top light is of a higher correlated color temperature, or more bluish, one while the side lights are of a lower temperature. This makes the (reflective) pads appear blue compared to the (diffusing) solder paste. Furthermore, it has been found that uniform or symmetrical lighting is provided by making the color of the light which projects onto the region of interest identical. Thus, in preferred embodiments the side lights are identical so that the overall symmetry is preserved.

The side light is provided having a central beam angle (i.e. the angle from the center of source or diffusing element) in the range of about 30 to about 60 degrees. Because of the high reflectivity of the metallic surfaces on the PCB, the intensity of the coaxial lighting is deliberately chosen to be lower than the side lighting (by a ratio of about 1% to 10%), as seen by the camera. Since the purpose of the top light is to provide illumination for the more reflective metallic features such as fiducials, pads, or leads, and since these surfaces reflect strongly, relatively less light is needed from the top. The side light provides illumination for the diffuse surfaces, which spread the light in all directions, so relatively more side lighting is needed. In short, there has to be a proper balance, else the metallic surfaces would be appear too bright (saturated) in the image while the diffusing surfaces would appear too dark.

The spectral distribution of the coaxial illumination is chosen to be significantly different from the spectral distribution of the side lighting. Preferred embodiments utilize correlated color temperature differences greater than about a thousand degrees. Alternatively, the difference could be characterized by using filters having sufficient differences in their spectral transmission characteristic. A third, more general, approach which can be used to characterize the color difference is to illuminate a spectrally neutral target with coaxial (top) and side light, in turn, and to compute ratios of the relative intensity of the top and the side illumination in the multiple spectral bands recorded by the camera, for example $R_{top}/R_{side}$, $G_{top}/G_{side}$, $B_{top}/B_{side}$; at least one of these ratios should be different from the others by about a factor of two or more.

This can be achieved in several ways, for example: lights of different correlated color temperatures, or lights of similar correlated color temperatures combined with different spectral band pass filters. This allows discrimination between the footprint pads (reflective) and the solder paste, which may or may not fully cover the pads, by measuring the spectral characteristic of the reflected light.

Having two types of lighting (i.e. central lighting and side lighting) also provides flexibility for adjustment of side lighting angle and relative intensity for better detection of orientation marks on components. This is achieved by viewing as many classes of orientation marks as possible and measuring the contrast between the marks and the component surface at several angles. Then decision is made as to the angle at which most or the most important marks have the greatest contrast.

The top light 22 may be provided as the type manufactured by RVSI NER DOAL-100-Fl or a Perkin-Elmer (EG&G) custom Xenon strobe flash. The side lights 24 may be provided as one of the types manufactured by Philips SLS 25 compact fluorescent (side light), or Stocker and Yale Superlight Model 18 dual fluorescent ringlight. Other lights such as Perkin-Elmer (EG&G) Xenon strobe flash may also be used. The Xenon strobe flash is based on Perkin-Elmer MVS-4000 and MVS-5000 products.

Several features of the optical system not found in prior art systems are believed to be: spectral discrimination through the combination of coaxial and side lighting, the use of diffuse side lighting to provide good spectral discrimination between components and PCB surface, and the use of coaxial lighting and side lighting with significantly different spectral distributions to provide good spectral discrimination between reflective surfaces (e.g., footprint pads) and diffusing surfaces (e.g., solder paste). Also, the use of coaxial lighting having an intensity which is a less than the intensity of the side lighting to further enhance the ability to discriminate between components and PCB surfaces is believed to not be found in prior art systems.

It should be appreciated that in accordance with the present invention, the imaging system 11 gathers information in the same field of view at the same time with the optic axis at right angles to object being inspected (e.g. the printed circuit board). In accordance with the present invention, the imaging system 11 with two different spectral distribution light sources is used, although it can also be achieved with two cameras, appropriate filters, and beamsplitters.

The imaging system 11 also comprises means for viewing as many classes of orientation marks as possible, means, coupled to said camera 12, for measuring the contrast between each of the orientation marks and the component surface at several angles; and means for determining the angle at which most or the most important orientation marks have the greatest contrast. The particular orientation marks to use can be defined by a user.

Figure 2:
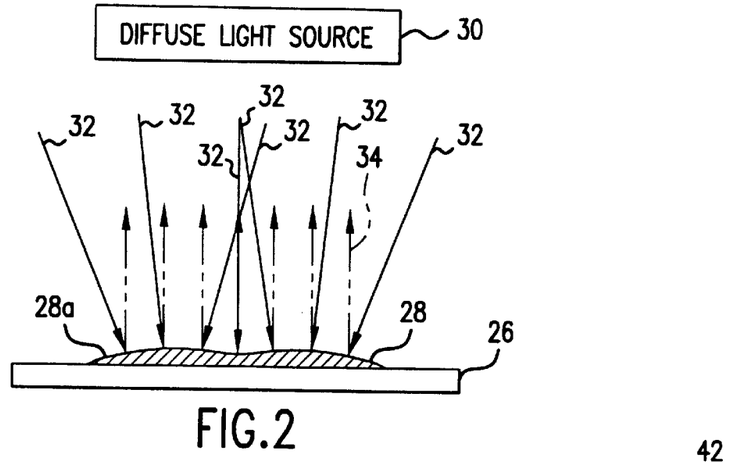
FIG. 2 is a diagrammatic side view of a printed circuit board having a fiducial with diffuse light projecting onto the fiducial from a region substantially above the fiducial.
Figure 3:
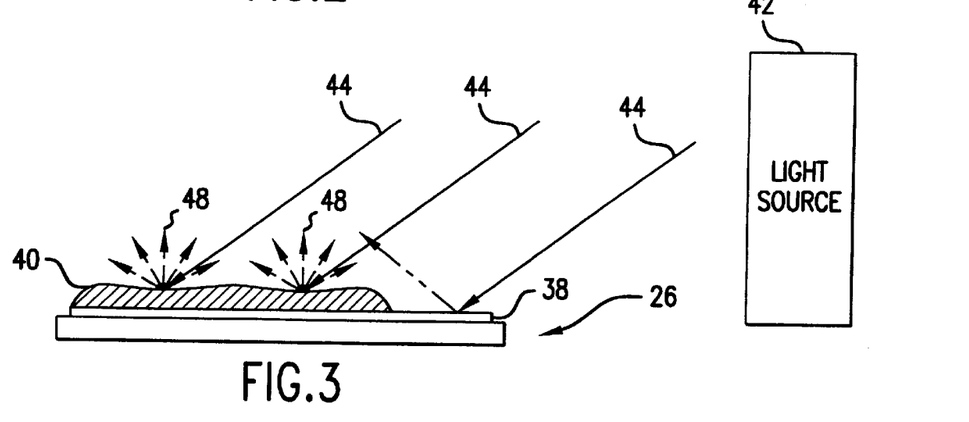
FIG. 3 is a diagrammatic side view of a printed circuit board having a pad and solder paste disposed thereon with diffuse light projecting onto the printed circuit board, pad and solder paste from a position substantially to the side of the printed circuit board.
Figure 4:
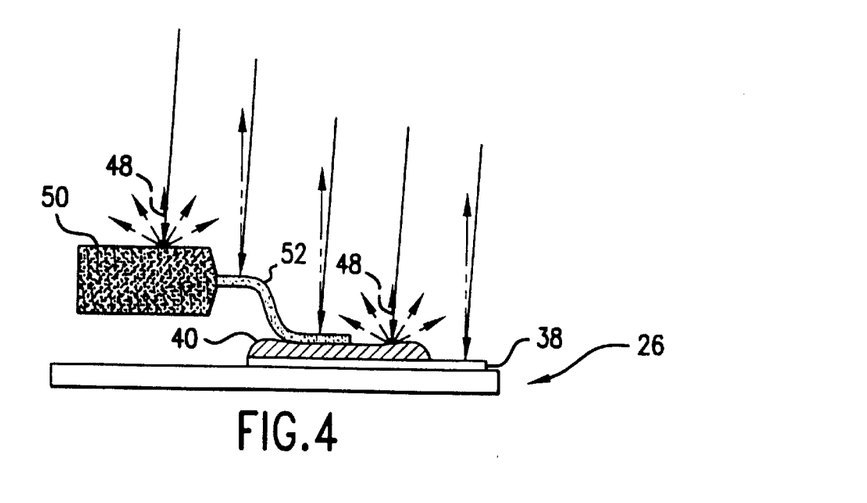
FIG. 4 is a diagrammatic side view of a printed circuit board having a pad, solder paste and a circuit component with a lead disposed thereon with light reflections from a first light source above the printed circuit board.

FIGS. 2, 3, and 4 illustrate the different effects of top and side illumination on fiducials, solder paste and metal pads on the printed circuit board.

Referring now to FIG. 2, a portion of a printed circuit board 26 is shown having a fiducial 28 disposed thereon. A diffuse light source 30 disposed above the PCB 26 and fiducial 28 projects a diffuse light (indicated by solid lines designated 32) on to the PCB 26 and fiducial 28. Since the surface 28a of the fiducial 28 is wavy and mirror-like (specular), light from the light source 30 must be directed downward with a spread of angles (as indicated by the solid lines 32) to ensure that at least some light is incident at such an angle so that the reflection goes straight upward toward the imaging system.

Portions of the light which impinge on the surface 28a of the fiducial 28 are reflected off the surface 28a and are directed directly at the camera (indicated by broken lines designated 34).

Referring now to FIG. 3, the printed circuit board portion 26 has a metal pad 38 having solder paste 40 disposed over a portion thereof. A side light source 42 projects a light (indicated by solid lines designated 44) on to the PCB 26, the pad 38 and the solder paste 40. Since the pads 38 are specular, the side light provided by light source 42 will be reflected away from the camera lens as indicated by line 39. On the other hand, the paste 40 is diffusing, so that some of the side light 44 will travel toward a camera lens (not shown) as indicated by dash lines 48. Thus, FIG. 3 illustrates the effect of lighting solder paste and pads using a light source positioned on the side of the area to be lit.

Referring now to FIG. 4, the PCB portion 26 has the pad 38 having the solder paste 40 disposed over a portion thereof and a circuit component 50 having a lead 52 disposed on the solder paste 40. Although the side light such as shown in FIG. 3 as light source 42 is not shown in the figure, it will have the following effect: Since the pads 38 and leads 52 are specular, the side light will be reflected away from the camera lens; on the other hand, the paste 40 and the circuit component 50 are diffusing, so that some of the side light 44 will travel toward the camera lens.

The specular surfaces (pads 38 and leads 52) thus strongly reflect the top light back into the camera lens (not shown). On the other hand, only some of light from the diffusing surfaces (paste 40 and component 50) will be directed back toward the camera lens. Thus, FIG. 4 illustrates the effect of top light on the component surface and its leads, on paste, and on pads.

Considering the combination of the effects of the side and top light together with the conditions that the top light be a small fraction of the side light, and that the top light has a different spectral distribution (say, bluish) from the side light, it has been recognized in accordance with the present invention that the light reaching the camera from the reflective surfaces (leads and pads) will have come only from the top light (with its bluish tint) and so will appear blue. The light reaching the camera from the diffusing surfaces will come mainly from the side light (since the amount of top light is small compared to the side light). Further, the spectral balancing of the camera's multiple spectral band pass sensitivities will have been carried out with a diffusing target where the side light dominates, further enhancing the apparent blueness of the reflecting surfaces.

The phenomenon of spectral differentiation of components 50 from the board surface 26 is also somewhat complex. If the components in question are generally gray in color, while board surfaces are almost always provided having a color other than gray (predominantly green), measurements show that lighting from the top could make a green board surface appear gray, while lighting from the side preserved the greenness of green boards.

It is believed that the explanation for this lies in the partially reflective surface of boards, and that the component of specular reflection from it does not convey color information; hence top lighting can make the board surface appear desaturated and grayish. On the other hand, diffuse light from the side lighting toward the camera does convey the color content of the board or component.

Having described preferred embodiments of the invention, it will now become apparent to one of ordinary skill in the art that other embodiments incorporating their concepts may also be used. It is felt therefore that these embodiments should not be limited to disclosed embodiments but rather should be limited only by the spirit and scope of the appended claims.

All publications and references cited herein are expressly incorporated herein by reference in their entirety.

What is claimed is:

1. A system for inspecting an object, the system comprising:
   (a) an imaging system having a field of view coincident with the object; and
   (b) a lighting system disposed about said imaging system, said lighting system including:
      (1) a first light source for providing in the field of view a first diffuse light having a first spectral distribution, the first diffuse light provided along an optical path coincident with an optical axis of said imaging system; and
      (2) one or more second light sources disposed about the object, each of said one or more second light sources substantially uniformly distributed rotationally about the optical axis and each of said second light sources for providing a second diffuse light which is substantially uniform in the field of view, each of said one or more second light sources disposed to provide the second diffuse light along optical paths which are at a predetermined angle with respect to the optical axis of said imaging system and having a second spectral distribution which is different from the first spectral distribution, and wherein the light provided by the first light source is more diffuse than the light provided by the one or more second light sources.

2. The system of claim 1 wherein said imaging system is a multi-spectral band pass imaging system.

3. The system of claim 2 wherein said multi-spectral band pass imaging system includes a telecentric lens.

4. The system of claim 3 wherein said multi-spectral band pass imaging system further includes an electronic camera coupled to said telecentric lens.

5. The system of claim 2 wherein said multi-spectral band pass imaging system includes lens means for reducing changes in magnification with the height of the object viewed.

6. The system of claim 1 further comprising a reflector/transmitter disposed along the optical axis of said imaging system and wherein said first light source projects the first diffuse light against the reflector/transmitter and said reflector/transmitter reflects the first diffuse light along the optical axis of said imaging system toward the object.

7. The system of claim 1 wherein said one or more second light sources are symmetrically disposed about the optical axis of said imaging system.

8. The system of claim 1 wherein said the first light source and each of the one or more second light sources provide spectral discrimination between reflective surfaces of the object and diffusing surfaces of the object.

9. The system of claim 1 wherein said one or more second light sources are disposed in a pattern corresponding to one of a regular polyhedron pattern; a quadrangular pattern; and a circular pattern.

10. The system of claim 9 wherein said one or more second light sources are disposed to the side of the optical axis of said imaging system at the predetermined angle in the range of about 30 degrees to about 60 degrees with respect to the optical axis.

11. The system of claim 1 wherein the intensity of each of the first and the one or more second light sources is selected such that the levels of light reflected from the surface being inspected can be sensed by the imaging system.

12. The system of claim 1 wherein the spectral difference between the first and the one or more second light sources is characterized by a correlated color temperature difference in the range of about 2700° K. to about 5100° K.

13. The system of claim 1 wherein each of the first and the one or more second light sources projects substantially the same spectral distributions onto the object.

14. The system of claim 1 wherein the one or more second light sources are provided having a central beam angle in the range of about 30 to about 60 degrees.

15. The system of claim 1 wherein the intensity of the first light source is selected to be less than the intensity of the one or more second light sources.

16. The system of claim 15 wherein the intensity of the first light source is selected to be less than the intensity of the one or more second light sources by a ratio of about one percent to about ten percent as seen by the imaging system.

17. The system of claim 1 wherein the difference between the spectral distribution of the first light source and the spectral distribution of the one or more second light sources is greater than a few hundred degrees.

18. The system of claim 1 wherein the difference between the spectral distribution of the first light source and the spectral distribution of the one or more second light sources is provided by using filters having differences in spectral transmission characteristics for each of the first and second light sources.

19. The system of claim 1 further comprising means for characterizing and computing the difference between the spectral distribution of the first light source and the spectral distribution of the one or more second light sources by the ratios of the relative intensity of the top and side illumination in multiple spectral bands recorded by the camera.

20. The system of claim 19 wherein said means for computing the ratios of the relative intensities of the top and side illumination comprise:
   (a) means for illuminating a spectrally neutral target with either the top or side lights;
   (b) means for measuring the relative amount of each spectral band seen by the camera; and
   (c) means for computing the ratio of each spectral band to the others.

21. The system of claim 19 wherein said means for computing ratios of the relative intensities of the top and side illumination means comprises means for combining lights of different correlated color temperatures or lights of similar correlated color temperatures with different spectral transmission filters.

22. The system of claim 1 further comprising:
   means for viewing as many classes of orientation marks as possible;
   means for measuring the contrast between each of the orientation marks and the component surface at several angles; and means for determining the angle at which most or the most important orientation marks have the greatest contrast.

23. The system of claim 1 wherein the first light source and each of the one or more second light sources are provided as strobe flash lights.

24. The system of claim 1 wherein each of the one or more second light sources are provided as one of (1) a compact fluorescent light; (2) a fluorescent ringlight; and (3) a strobe flash light.

25. The system of claim 1 wherein the characteristics of said first light source and each of the one or more second light sources provides spectral discrimination between the object being inspected and at least one other object.

26. The system of claim 1 wherein said imaging system gathers information in the same field of view at the same time with the optical axis at right angles to object being inspected.

27. The system of claim 1 wherein said first light source is a different spectral distribution light source than each of the one or more second light sources.

28. The system of claim 27 wherein:
   the first light source is at a correlated color temperature of about 5100 degrees K.; and
   each of the one or more second light sources is at a correlated color temperature of about 2700 degrees K.

29. An optical system for inspecting a printed circuit board, the system comprising:
   (a) a multi-spectral imaging system including:
      (1) a multi-spectral camera having an optical axis; and
      (2) a telecentric lens coupled to said multi-spectral camera; and
   (b) a lighting system disposed about said imaging system, said lighting system including at least one coaxial light source and at least one side light source with the coaxial light source and the at least one side light source having relative spectral distributions, relative light intensities and relative diffuseness characteristics selected to enhance spectral discrimination and to enhance contrast between metallic surfaces disposed on the printed circuit board and a printed circuit board surface, wherein the intensity of said coaxial light source is selected to be less than the intensity of said at least one side light source.

30. The system of claim 29 wherein:
   said coaxial light source illuminates metallic surfaces disposed on the printed circuit board; and
   one or more side light sources are disposed to the side of the optical axis and provide diffuse light and wherein said coaxial and side light sources uniformly light a region of the printed circuit board being inspected.

31. The system of claim 30 wherein said at least one side light source is symmetrically disposed about the optical axis.

32. The system of claim 31 wherein said at least one side light source is disposed in a pattern corresponding to one of: a regular polyhedral pattern; a quadrangular pattern and a circular pattern.

33. The system of claim 29 wherein said coaxial light source is more diffuse than said at least one side light source.

34. The system of claim 29 wherein the intensity of said coaxial light source and the intensity of said at least one side light source are selected such that the levels of light reflected from the surface being inspected can be sensed by said camera.

35. The system of claim 29 wherein said coaxial light source has a different spectral distribution than said at least one side light source.

36. The system of claim 29 wherein each of the lights projects substantially the same spectrally distributed light onto the region of interest.

37. The system of claim 29 wherein the intensity of the light provided by said coaxial light source is selected to be less than the intensity of the light provided by said at least one side light source by a ratio of about one percent to about ten percent as detected by the camera.

38. The system of claim 29 wherein said coaxial light source is selected to provide a light having a spectral distribution which is different than the spectral distribution of the light provided by said at least one side light source.

39. The system of claim 29 further comprising:
   means for viewing as many classes of orientation marks as possible;

means for measuring the contrast between each of the orientation marks and the component surface at several angles; and means for determining the angle at which predetermined ones of the orientation marks have a predetermined level of contrast.

40. The system of claim 29 wherein said imaging system gathers information in the same field of view at the same time with the optical axis at right angles to the object being inspected.

* * * * *

UNITED STATES PATENT AND TRADEMARK OFFICE
CERTIFICATE OF CORRECTION

PATENT NO.    : 6,552,783 B1
DATED         : April 22, 2003
INVENTOR(S)   : Peter E. Schmidt et al.

It is certified that error appears in the above-identified patent and that said Letters Patent is hereby corrected as shown below:

Column 2,
Line 1, delete "light to used" and replace with -- light to use --.

Column 4,
Line 47, delete "distributons" and replace with -- distributions --.

Column 5,
Line 9, delete "or other object or device" and replace with -- or other objects of devices --.
Line 26, delete "inspected,: where" and replace with -- inspected, where --.
Line 47, delete "telecentric properties lens since" and replace with -- telecentric properties since --.

Column 6,
Line 31, delete "back). n other" and replace with -- back)). In other --.

Column 7,
Line 24, delete "more bluish, one while" and replace with -- more bluish, while --.
Line 45, delete "would be appear" and replace with -- would appear --.

Column 8,
Line 10, delete "Then decision" and replace with -- Then a decision --.
Line 31, delete "which is a less" and replace with -- which is less --.

UNITED STATES PATENT AND TRADEMARK OFFICE
CERTIFICATE OF CORRECTION

PATENT NO.    : 6,552,783 B1
DATED         : April 22, 2003
INVENTOR(S)   : Peter E. Schmidt et al.

It is certified that error appears in the above-identified patent and that said Letters Patent is hereby corrected as shown below:

<u>Column 11,</u>
Line 61, delete "one of (1) a" and replace with -- one of: (1) a --.
Line 54, delete "; and means" and replace with -- ; and
                                                                means --.
Lines 55 and 56, delete "most or the most important orientation marks have the greatest contrast" and replace with -- predetermined ones of the of the orientation marks have a predetermined level of contrast --.

Signed and Sealed this

Twenty-fifth Day of November, 2003

JAMES E. ROGAN
*Director of the United States Patent and Trademark Office*